US00PP14506P29

(12) United States Plant Patent
van der Kraan-Zonderland

(10) Patent No.: US PP14,506 P2
(45) Date of Patent: Feb. 3, 2004

(54) GYPSOPHILA PLANT NAMED 'SUMMER SNOW'

(50) Latin Name: *Gypsophila hybrida*
Varietal Denomination: Summer Snow

(75) Inventor: Maria Francisca Theresia van der Kraan-Zonderland, Delft (NL)

(73) Assignee: Astee Flowers, B.V., Nieuwveen (NL)

( * ) Notice: Subject to any disclaimer, the term of this patent is extended or adjusted under 35 U.S.C. 154(b) by 0 days.

(21) Appl. No.: 10/303,438

(22) Filed: Nov. 25, 2002

(51) Int. Cl.[7] ..... A01H 5/00
(52) U.S. Cl. ..... Plt./354
(58) Field of Search ..... Plt./354

*Primary Examiner*—Bruce R. Campell
*Assistant Examiner*—June Hwu
(74) *Attorney, Agent, or Firm*—C. A. Whealy

(57) ABSTRACT

A distinct cultivar of Gypsophila plant named 'Summer Snow', characterized by its compact, upright and outwardly spreading plant habit; freely flowering habit; many-petalled white-colored flowers arranged in compact and dense compound cymes; and good post-production longevity.

1 Drawing Sheet

Botanical classification/cultivar designation: Gypsophila hybrida cultivar Summer Snow.

BACKGROUND OF THE INVENTION

The present Invention relates to a new and distinct cultivar of Gypsophila plant, botanically known as Gypsophila hybrida, grown commercially as a potted or landscape plant, and hereinafter referred to by the name 'Summer Snow'.

The new Gypsophila is an induced mutation of an unidentified proprietary selection of Gypsophila hybrida, not patented. The proprietary selection is the product of a open-pollination of Gypsophila hybrida Iron Gypsophila as the female, or seed, parent, not patented, and an unknown cultivar as the male, or pollen parent. Cuttings from chemically treated plants were planted and the new Gypsophila was discovered and selected by the Inventor in 1998 in a controlled environment in Delft, The Netherlands, as a single flowering plant among a population of plants. Plants of the new Gypsophila differed from plant of the proprietary selection in flower size and inflorescence form.

Asexual reproduction of the new Gypsophila by cuttings taken at Delft, The Netherlands, has shown that the unique features of this new Gypsophila are stable and reproduced true to type in successive generations.

SUMMARY OF THE INVENTION

The following traits have been repeatedly observed and are determined to be the unique characteristics of 'Summer Snow'. These characteristics in combination distinguish 'Summer Snow' as a new and distinct cultivar:

1. Compact, upright and outwardly spreading plant habit.
2. Freely flowering habit.
3. Many-petalled white-colored flowers arranged in compact and dense compound cymes.
4. Good post-production longevity.

In side-by-side comparisons conducted in Delft, the Netherlands plants of the new Gypsophila are more compact and have more compact and denser cymes than plants of Iron Gypsophila. In side-by-side comparisons conducted in Delft, the Netherlands, plants of the new Gypsophila have shorter and narrower leaves, smaller flowers, stronger flower stems, and more compact cymes than plants of the cultivar Magic Golan disclosed in U.S. Plant Pat. No. 9,257.

Plants of the new Gypsophila differ from plants of the Gypsophila cultivar Blancanieves, disclosed in a U.S. Plant patent application Ser. No. 10/303,495 filed concurrently, primarily in plant habit as plants of the cultivar Blancanieves are taller and typically grown as cut flowers.

The cultivar Summer Snow has not been observed under all possible environmental conditions. The phenotype may vary somewhat with variations in environment such as temperature and light intensity, without, however, any variance in genotype.

BRIEF DESCRIPTION OF THE PHOTOGRAPH

The accompanying colored photograph illustrates the overall appearance of the new Gypsophila, showing the colors as true as it is reasonably possible to obtain in colored reproductions of this type. Colors in the photograph may differ slightly from the color values cited in the detailed botanical description which accurately describe the colors of the new Gypsophila.

The photograph comprises a side perspective view of a typical flowering plant of the new Gypsophila.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe four-month old plants grown in two-liter containers during the autumn in Ter Aar, The Netherlands, in a glass-covered greenhouse with day temperatures about 20° C. and night temperatures about 16° C.

Botanical classification: Gypsophila hybrida cultivar Summer Snow.

Commercial classification: Potted plant Gypsophila.

Parentage: Induced mutation of an unidentified proprietary selection of Gypsophila hybrida, not patented.

Propagation:

*Type.*—By cuttings.

*Time to initiate roots.*—Summer: About 21 to 30 days at a temperature of 22° C. Winter: About 26 to 34 days at a temperature of 18° C.

*Root description.*—Fine and well-branched.

Plant description:

*Appearance.*—Perennial potted or landscape plant. Compact, upright and outwardly spreading; broadly inverted triangular form. Freely flowering; many-petalled white-colored flowers arranged in compact and dense compound cymes. Moderate growth habit.

*Branching habit.*—Freely branching; about six lateral branches develop.

*Plant height.*—About 35 cm.

*Plant width.*—About 60 cm.

*Lateral branch length.*—About 25 cm.

*Lateral branch diamter.*—About 3.5 mm.

*Internode length.*—About 2.1 cm.

*Strength.*—Strong.

*Stem texture.*—Glabrous.

*Stem color.*—143B to 143C.

*Foliage description.*—Arrangement: Opposite; sessile. Shape: Lanceolate to narrowly lanceolate. Apex: Acute. Base: Cuneate. Margin: Entire. Length: About 4 cm. Width: About 1.1 cm. Texture: Glabrous; slightly leathery. Venation pattern: Parallel. Color: Young and fully expanded leaves, upper surface: 137A. Young and fully expanded leaves, lower surface: 137B. Venation, upper surface: 143A. Venation, lower surface: 143B.

Flowering description:

*Appearance.*—Upright, compact and dense compound cymes with numerous many-petalled white-colored flowers, flowers rotate; about 80 flowers per inflorescence. Flowers face upright to slightly outwardly.

*Flowering response.*—Under outdoor conditions, plants flower from June through September.

*Post-production longevity.*—Good, flowers last for more than 10 days. Inflorescences persistent.

*Fragrance.*—Strong; sweet and pleasant.

*Inflorescence length.*—About 25 cm.

*Inflorescence width.*—About 30 cm.

*Inflorescence bud.*—Shape: Flattened globular. Length: About 2 mm. Diameter: About 1.5 mm. Color: 155C.

*Flower diameter.*—About 6 mm.

*Flower depth* (*height*).—About 5 mm.

*Petals/petaloids.*—Quantity per flower: About 25. Shape: Obovate to narrowly obovate. Apex: Rounded. Base: Attenuate. Margin: Entire. Length: About 3 to 3.5 mm. Width: About 1 to 1.5 mm. Texture: Smooth, glabrous. Color: When opening, upper and lower surfaces: Closest to N155A. Mature, upper and lower surfaces: Closest to N155A; color becoming closer to 199D with development.

*Sepals.*—Quantity per flower: About five. Shape: Narrowly elliptic. Apex: Acute. Base: Cuneate. Margin: Entire. Length: About 2 mm. Width: About 1 mm. Color: Immature and mature, upper surface: 141B. Immature and mature, lower surface: 137B.

*Peduncle.*—Strength: Strong. Length: About 1.9 cm. Diameter: About 1 mm. Angle: About 5 to 40° from vertical. Texture: Smooth. Color: 143B to 143C.

*Pedicels.*—Strength: Moderately strong. Length: About 5 mm. Diameter: About 0.3 mm. Angle: About 5 to 40° from vertical. Texture: Smooth. Color: 143C.

*Reproductive organs.*—Stamens: Most of the stamens are transformed into petaloids; typically about two to six "true" stamens observed. Anther shape: Basifixed; almost orbicular, flattened. Anther length: About 0.1 mm. Anther color: Close to 167C. Pollen: None detected. Pistils: Quantity per flower: About two. Style length: About 4 mm. Style color: 157B to 157C. Pistil length: About 4 mm. Stigma color: 157C to 157D. Ovary color: 143A to 143B.

*Seed/fruit development.*—Seed and fruit development has not been observed.

Disease/pest resistance: Plants of the new Gypsophila have not been observed to be resistant to pathogens and pests common to Gypsophilas.

It is claimed:

1. A new and distinct cultivar of Gypsophila plant named 'Summer Snow', as illustrated and described.

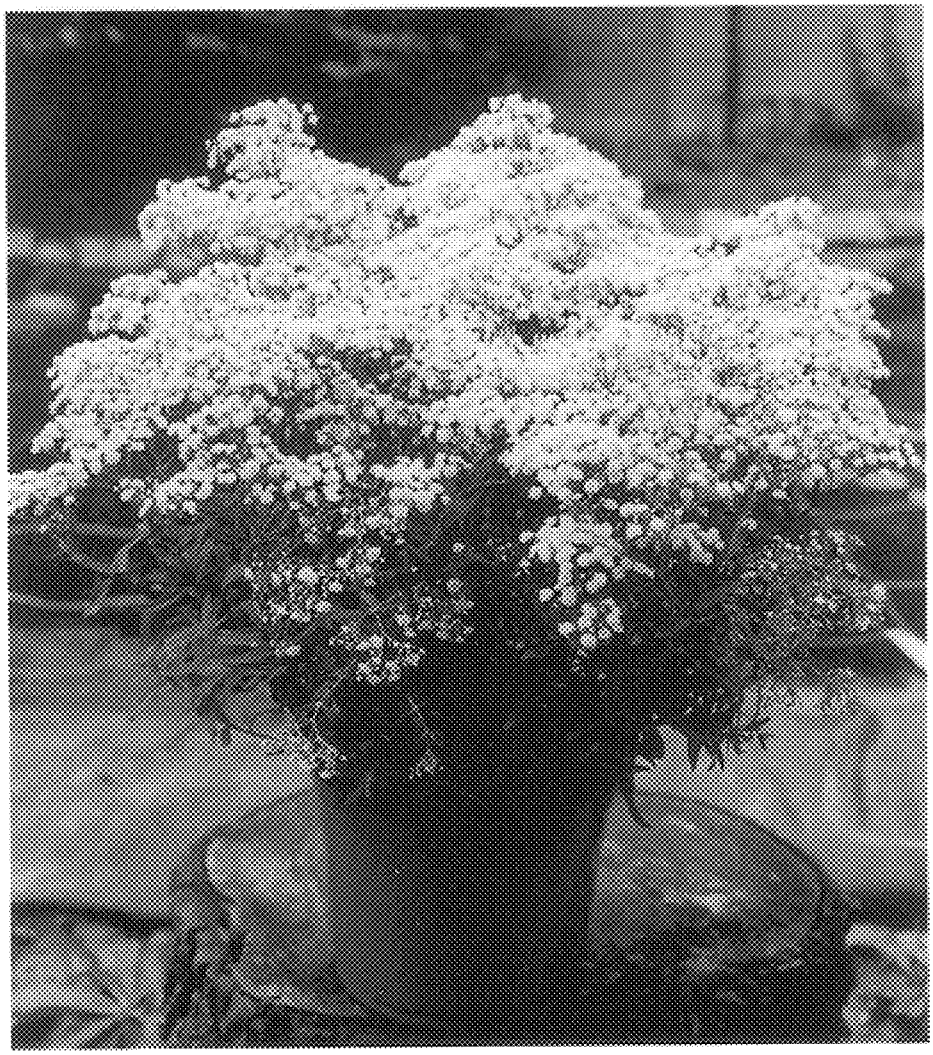

* * * * *